United States Patent [19]

Wolbarsht

[11] 4,155,632
[45] May 22, 1979

[54] METHOD AND APPARATUS FOR TESTING VISION

[75] Inventor: Myon L. Wolbarsht, Durham, N.C.

[73] Assignee: Acadia Associates, Durham, N.C.

[21] Appl. No.: 661,807

[22] Filed: Feb. 26, 1976

[51] Int. Cl.² .................... A61B 3/02; A61B 3/00
[52] U.S. Cl. .................... 351/36; 351/33; 351/39; 351/25
[58] Field of Search .............. 351/36, 31, 17, 39, 351/33, 34, 132, 8, 25, 32

[56] References Cited

U.S. PATENT DOCUMENTS

| | | | |
|---|---|---|---|
| 1,437,809 | 12/1922 | Jones | 356/232 |
| 1,647,017 | 10/1927 | Reaves | 351/34 |
| 2,294,382 | 9/1942 | Burian | 351/25 |
| 2,422,384 | 6/1947 | Alexander | 351/33 |
| 2,567,003 | 9/1951 | Wottring | 351/36 |
| 2,674,153 | 4/1954 | Alexander | 351/36 |
| 3,469,904 | 9/1969 | Allen | 351/32 |
| 3,684,355 | 8/1972 | Molner | 351/36 |
| 3,814,510 | 6/1974 | Adler | 351/36 |
| 4,027,954 | 6/1977 | Good | 351/36 X |

FOREIGN PATENT DOCUMENTS 2321570  11/1974  Fed. Rep. of Germany ............. 351/36

OTHER PUBLICATIONS

Matthew Luckiesh, Test Charts Representing a Variety of Visual Tasks, Mar. 1944, pp. 270-274, Amer. Jour. of Opht.

Primary Examiner—Paul A. Sacher
Assistant Examiner—Rodney B. Bovernick
Attorney, Agent, or Firm—Kenyon & Kenyon

[57] ABSTRACT

The disclosure relates to a method and apparatus for testing eyesight in the presence of controlled varying degrees of contrast at a target which is being viewed. The contrast ratio of the illumination of the portion of a target having a series of test patterns with respect to the illumination of the background of the target surrounding the patterns affects intraocular light scattering in a subject's eyes. In one disclosed embodiment an eye chart is provided which has opaque symbols on an illuminated background. By means of a transparent surface which is partly reflective, such as a half-silvered mirror, a veiling light is superimposed uniformly upon the light transmitted from the illuminated background of the target toward the subject's eyes. By varying the level of the background light or the veiling light or the darker (polarized) portions of the target pattern with a polarizing filter, or all, different contrast ratios of the light directed from the location of the target toward the subject's eyes can be presented. The disclosure additionally relates to the measurement of the effect of varying contrast ratios of a target on a subject's eyes by the use of a plurality of different charts, each having a background and a pattern thereon which provide a different contrast ratio to the subject's eyes.

22 Claims, 7 Drawing Figures

METHOD AND APPARATUS FOR TESTING VISION

BACKGROUND OF THE INVENTION

1. Field of the Invention

The invention pertains to the art of testing eyesight and more in particular to the art of testing eyesight under different conditions of the contrast ratio of a target presented to the test subject. The invention also pertains to the art of measuring visual performance of a subject on targets of varying contrast ratios, i.e. when the ratio of dark to light in the test object of the target is varied. The invention additionally pertains to the art of testing the fusion potential (binocular single image) of a subject's eyes under different conditions of the contrast ratio of the target presented to the test subject. The invention further pertains to the art of determining glare sensitivity of a subject's eyes.

2. Description of the Prior Art

U.S. Pat. No. 2,209,728 which issued to H. R. HIGLEY on July 30, 1940, discloses a device for measuring a subject's sensitivity to glare. Light from a dazzling brilliant light source is focused by a reflector directly onto the eyes of a subject who views the brilliant source in an initially totally darkened chamber. A controllable light source which is off-set and in front of the dazzling light source is then directed at objects (such as letters painted dull white) which are in the vicinity of the dazzling light source. The intensity of this controllable source is then increased until the viewer is able to see the objects in the presence of the glare of the source. The value of the intensity of the controllable dazzling source when the objects just become visible is a measure of the glare sensitivity of the viewer.

There is no disclosure in this patent of an arrangement for directing toward the subject a level of glare light extending uniformly across the field of view.

U.S. Pat. No. 3,684,355 which issued to S. F. MOLNER on Aug. 15, 1972 relates to another glare sensitivity measuring device. Light from a glare source is directed in pencil-beam fashion at a viewer through a variable density filter which permits controlling of the intensity of the glare light reaching the viewer. Out of the path of the glare source but within the field of vision of the viewer, a target is arranged. The target is illuminated by another light source arranged in back of the target. A variable density background filter arranged between the target and the viewer controls the intensity of the illumination from the target reaching the viewer. In this apparatus, the relative intensity of the light from the glare source to the intensity of the target illumination is controlled by varying the density of the background filter while maintaining the light from the glare source constant, by varying the intensity of the glare source while maintaining the density of the background filter constant, or by varying both. Here again there is no disclosed construction for directing toward the viewer a level of glare light which extends uniformly across the field of view.

In U.S. Pat. No. 1,437,809 which issued to L. A. JONES on Dec. 5, 1922 there is disclosed apparatus for measuring the visibility of an object with respect to its background such as the visibility against the sea and sky of a marine vessel which has been camouflaged by appropriate painting of its outer surface. The apparatus includes a telescope for enabling the user to view the object such as a camouflaged marine vessel. A semi-transparent mirror extends across the optical axis of the telescope in a position adapted to reflect light in the form of a veiling light from a lamp source toward the user's eye. The composite brightness resulting from the veiling light and the light reflected from the observed object is preferably maintained substantially constant by decreasing the ligh from the object and increasing the veiling light or vice versa. Since the device of this patent was not disclosed as being related to vision testing, the device was taught as operating with constant composite brightness with the stated purpose that this condition would eliminate any change of light level at the user's eyes and thereby prevent the user's eyes from interfering with the visibility condition being measured. It now has been discovered in accordance with the invention that the user's eyes will interfere with the visability condition being measured even when composite brightness is constant if the contrast ratio changes.

In U.S. Pat. No. 2,799,203 which issued to W. R. Kerr on July 16, 1957, apparatus is described for determining the degree of gloss of a finished surface. In this apparatus, the image of a mask comprising a background upon which are disposed rows of black letters of varying size is projected onto successive finished surfaces each having a different degree of gloss. A subject person observing the projected images thus sees images having different degrees of contrast between their rows of letters and their backgrounds. The surfaces of higher gloss have a higher contrast between the letters and background while those of lower gloss have a lower contrast. The different degrees of contrast give a relative measure of the different degrees of gloss of the surfaces.

It is known in the prior art to measure the fusion potential of a subject's eyes by means of a stereoscopic viewer which is adapted to direct each of the test subject's eyes to a different one of a pair of adjacent eye charts having dissimilar targets. With fused vision, the two targets are viewed by the subject as a single fused target. The stereoscopic viewer is provided with optical wedges which can be adjusted to displace the line of sight of the subject's eyes from a condition in which the targets appear fused. The ability of the subject to overcome the displacement of his line of sight by the optical wedges and then sense a fused image is indication of the subject's fusion potential. Progressively increasing the degree of displacement of the line of sight, in the measuring of the ability of the subject to again sense fused targets, enables a discrete determination of the fusion potential to be made.

SUMMARY OF THE INVENTION

In accordance with the method and apparatus of the invention a target having test patterns thereon is presented to the eye. The test patterns taken with the background of the target present varying contrast ratios which enable the eye being tested to be compared to the performance of a "normal" eye for the same patterns. The vision tester of the invention can be used as a "cataract tester" since it is capable of measuring intraocular light scattering caused by a cataract condition. Here it should be noted that other eye abnormalities can cause such light scattering. Of course, ophthalmoscopic examination would be necessary in order to relate measurements obtained by use of the vision tester of the invention to a particular pathological condition.

In accordance with the invention there is provided an eye chart having black letters on a white translucent background. The eye chart is illuminated from the side opposite to that bearing the letters with the result that the dark letters compare in contrast to the white illuminated background. Since the vision tester of the invention is intended to measure visual performance of the eye on targets of varying contrast ratios, the range of contrast ratios between the brightness of the letter compared to that of the illuminated background can be varied. A veiling light is superimposed upon the light being directed from the eye chart toward the eye of the subject. The brightness of the veiling light is added both to the illuminated background and the black letters of the eye chart. Means are provided for varying the intensity of either the background illumination of the chart, the veiling light, or both in order to provide a range of different contrast ratios. In the preferred embodiment the intensity of the veiling light is varied.

Any condition within the eye such as a cataract condition which can scatter light within the eye serves to decrease the contrast ratio of the target being viewed since the scattered light increases the light level in the dark parts of the target being used. It is known that normal eyes have some internal light scattering. As a result a subject with normal sight can read a given line of an eye chart with no veiling light while a certain amount of veiling light will reduce the visual acuity of the subject. By way of example, a given level of background illumination of the chart, the contrast of the chart (ratio of black to white), the veiling light or all can reduce the visual acuity from 20/20 to 20/30. The vision tester of the invention is designed to measure the difference between the visual acuity of a person with pathological light scattering in his eyes as compared to the visual acuity of a person having normal vision.

The vision tester of the invention can also be used to test the fusion potential of a subject's eyes, that is to say the ability of the eyes to fuse dissimilar objects or, more simply stated, the ability to use both eyes as one. A binocular version of the vision tester of the invention can be used to assess the amount of fusion potential of the eyes under various contrast ratios. The binocular version provides viewing of an adjacent pair of eye charts having dissimilar targets. Optical wedges in the viewer of the binocular version enable the line of sight of the subject to be displaced to the extent that the subject must exert some degree of effort to sense a fused image of the targets. It is known that the fusional ability of the eyes is to an extent dependent upon the contrast ratio of the scene being viewed. Upon reducing the contrast ratio it is known that a point is reached at which the eyes become incapable of fusing dissimilar objects and accordingly the ability of the eyes to act as one ceases. Once the optical wedges have been set to displace the line of sight, they are no longer adjusted. The vision tester is operated to provide progressively increasing levels of veiling light. A point will be reached at which the progressive reduction of the control ratio of the targets as seen by the subject will cause the fusion potential of the subject to be exceeded. At this point, the subject can no longer see a fused image. The lack of fusion can be detected when the subject reports that two separate images are seen, or the examiner visually observes that the subject's eyes do not diverge, or by optical detectors of the change in corneal reflection, or by electrical measurements of the position of the eyes or by various combinations of these.

In addition the vision tester of the invention can be used to measure glare sensitivity of the subject's eyes since this phenomenon at least in part is a function of the degree of intraocular light scattering.

In another embodiment of the invention a series of test charts having different contrast ratios under a standard lighting condition are provided. The targets present different contrast ratios to the subject as is done with the vision tester of the invention employing veiling light. The ability of a subject to read charts of reduced contrast is the basis of measuring light scattering or fusion potential of the test subject's eyes.

BRIEF DESCRIPTION OF THE DRAWINGS

The above and other features and aspects of the present invention will become more apparent upon reading the following detailed description in conjunction with the accompanying drawings, in which:

FIG. 3 is a schematic representation of a vertical section view of the apparatus of FIG. 1 and additionally includes a schematic view of variable sources of light used with the apparatus;

DESCRIPTION OF THE PREFERRED EMBODIMENTS

Figure 1:
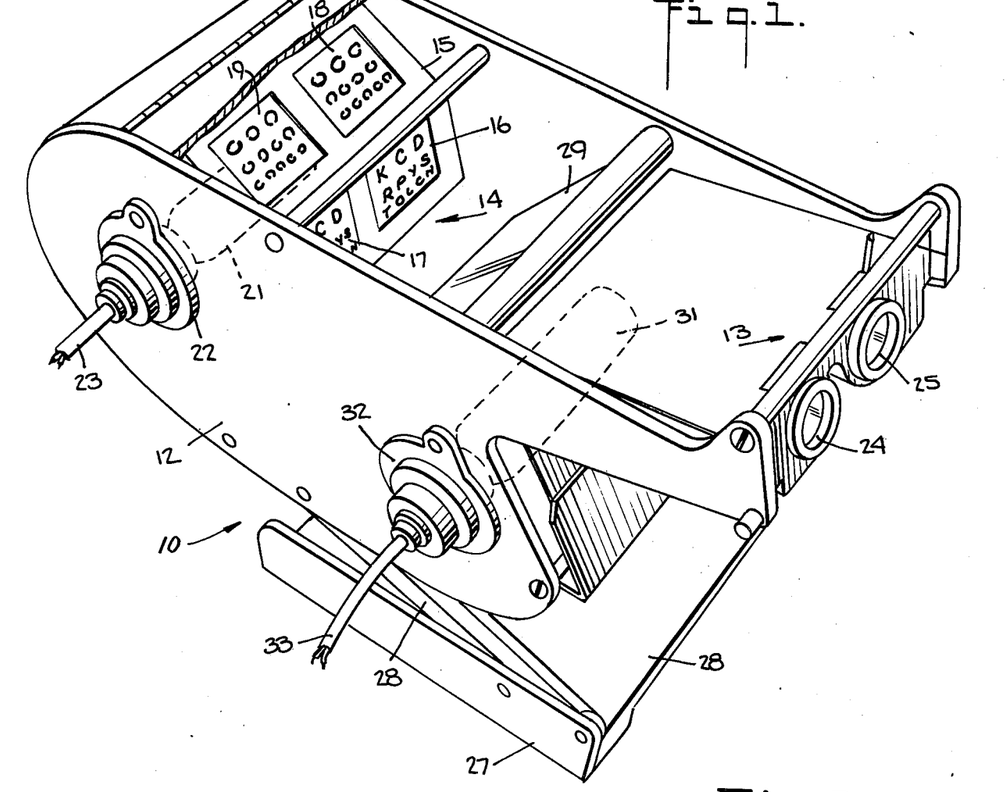
FIG. 1 is a perspective view of a vision testing apparatus in accordance with the principles of the invention.

FIG. 1 shows vision tester apparatus 10 in accordance with the principles of the present invention. As shown, vision tester 10 comprises a central body or enclosure 12 having in its frontal portion, a viewing assembly 13 and in its rearward portion a target assembly 14. The target assembly 14 includes a hollow hexagonal member or drum 15 which is rotatably supported within the housing. Each hexagonal surface of drum 15 supports a pair of corresponding targets in a side-by-side relationship. Target pair 16 and 17 and target pair 18 and 19 are specifically illustrated. Each of the supported targets, in turn, includes a plurality of opaque regions which are situated on a transparent or translucent background and which may take on the shape of any letter, number or other symbol. The opaque regions of the test targets 16 and 17 are horizontally extending rows of letters with the letters in each row having a different size. Thus each different row provides a different test of the visual acuity of the eyes of the subject being tested.

The regions on the targets 18 and 19, on the other hand, are illustrated as rows of broken rings of different size and orientation with the rings of corresponding rows of the two charts being unsymmetrical. The charts 18 and 19 can correspond to known eye charts which are used for testing the fusional potential (binocular single image) of a viewer's eyes.

Interior to the hexagonal drum 15 is a light source 21 shown in dotted line. The light source or lamp 21 is depicted as a cylindrically shaped light bulb which extends through the central portion of member 15, parallel to the hexagonal faces thereof. The light source 21 is supported in the housing by a threaded coupling 22 to which electrical energy is applied from a source (not shown) by way of lead 23. In FIG. 1, the drum 15 has been rotated to a position in which the surfaces thereof supporting the targets 16 and 17 is situated substantially in a vertical plane. This places the targets in alignment with the viewing assembly 13.

Viewing assembly 13 comprises two horizontally spaced eyepieces 24 and 25 through which the viewer observes the targets. The eyepieces and optics related thereto can be arranged to provide binocular vision where the subject is to view a single test target simultaneously with both eyes. The eyepieces and related optics can also be arranged to restrict the vision of each eye to a different one of a pair of targets. Thus, as shown in FIG. 3, assembly 13 can include a binocular optical assembly 41 having optics 42 and 43 adjacent eyepieces 24 and 25. The binocular optical assembly can include optical wedges or lenses (not shown) having cylinders. These lenses when rotated about the line of sight through their respective eyepieces enable the viewer's vision to be aligned properly with respect to the different targets in correspondence with the user's interpupillary distance. A mask 44 is rotatably supported at the center of the assembly 41 and can be rotated to block either of optics 42 and 43 and thereby prevent viewing therethrough whenever one eye is to be tested at a time.

With the mask 44 in its central position, the optics 42 and 43 cause the respective targets 16 and 17 aligned therewith to appear to the viewing eyes at the apertures 24 and 25 as a single, that is fused, image. Thus the optics serve to align the line of sight to each eye with a different one of test targets 16 and 17. In this position of mask 44, both eyes of the subject can be tested simultaneously. Rotating the mask 44 to either side position thereof blocks the respective optics 42 and 43, thereby permitting individual testing of either eye.

As seen in FIG. 1, the tester 10 includes a hinged top cover 26 which provides access to the interior of body 12 and prevents ambient light from impinging upon the target assembly 14. The tester is provided with a stationary base 27. Body 12 is adjustably supported on base 27 by a parallel linkage comprising uprights 28 which are pivotally mounted with respect to the body and the base. Support of the body portion 12 in this manner enables the body portion to be moved both horizontally and vertically to adjust the viewing assembly to accommodate the different positions of the eyes of different subjects.

The basic portions of the tester 10 comprising the body, the drum and lamp, the eyepiece and optics, and the adjustable supports generally correspond to those of conventional eye testing apparatus. Thus, typically, in the use of such apparatus, the viewer is stationed at the viewing assembly 13 with his or her eyes locking into the eyepieces 24 and 25. With the mask 44 at its central position, the lamp 21 is turned on, thereby illuminating the translucent background of each of the targets 16 and 17 which are in alignment with the assembly 13. The viewer, thus, is presented with a fused target whose field of view comprises the opaque symbol regions and the translucent background region. The viewer is then asked to read the opaque symbols until he reaches a line at which he can no longer discern all of the symbols. When this line is reached his visual acuity is thus established at the acuity associated with the previous line. If the viewer's eyes are then to be individually tested, the mask 44 is rotated and the procedure repeated separately for each of the right and left eyes.

As can be appreciated, in the aforesaid testing procedure, the level of illumination reaching the viewer from the opaque symbol regions is substantially zero and that from the translucent background region is at a constant level as determined by the intensity of lamp 21. The contrast ratio of the target being viewed is thus always at a substantially constant value which cannot be varied. As a result, with the apparatus of tester 10 without the provision of veling light in accordance with the invention, vision testing of the subject is only possible under a single contrast ratio condition and, hence, the eye conditions and eye performance discernible from testing under varying contrast ratio conditions cannot be ascertained.

In accordance with the invention, varying contrast ratio conditions are realized in the apparatus tester 10 by further including therein a further illumination means which provides an additional uniform illumination of the entire field of view of the target being observed. As shown in FIG. 1, the aforesaid illumination means comprises a half-transmitting half-reflecting means in the form of a semi-transparent or half-silvered mirror 29 which is disposed in the central portion of body 12 between the target assembly 14 and the viewing assembly 13. The mirror 29 is supported at an angle in body 12 with its upper portion inclined away from the target assembly. Half-silvered mirror 29 is sufficiently extensive to intercept the entire field of view of each of the adjacent pairs of targets on the face of the member 15 aligned with viewing assembly 13. Thus, the mirror is coextensive with the field view of the targets when viewed individually or fused from viewing assembly 13.

The illumination means for the half-silvered mirror includes a light source or lamp 31 in the form of a cylindrical electric lightbulb which is situated in the region below mirror 29. The source 31 is secured to the body by a coupling 32 from which extends a lead 33 for attachment to an electrical source of energy (not shown).

Figure 2:
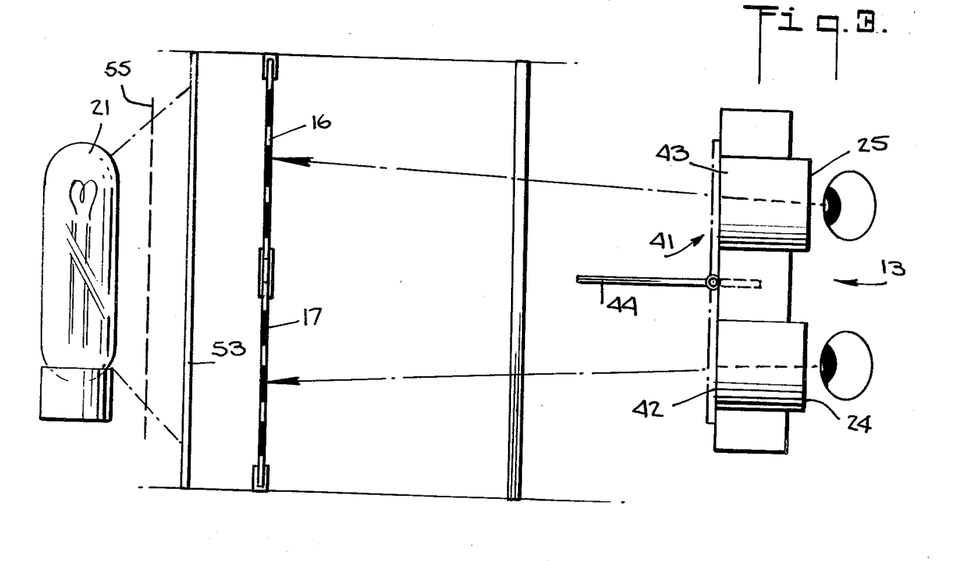
FIG. 2 is a fragmentary horizontal section view of the upper portion of the apparatus of FIG. 1 showing the provision of a binocular lens system for viewing a test target through veiling light.

The schematic diagram of FIG. 2 shows the positioning of mirror 29 with respect to the viewing assembly 13 and target assembly 14. As noted, the mirror 29 extends across the entire field of view of the targets 16 and 17 being viewed. As can be also seen from FIG. 2, the target assembly 14 and the illumination means 21 are each also provided with a diffusion screen such as a ground glass screen to provide more uniform distribution of light. Thus, target assembly 14 is provided with a diffusion screen 53 which is situated between the source 21 and targets 16 and 17. Likewise, the illumination means 31 is provided with a diffusion screen 54 situated between source 31 and mirror 29. Also shown in FIG. 2 are variable electrical sources 51 and 52 which control the level of illumination of the sources 21 and 31, respectively. These sources can comprise an electrical power control which supplies an adjustable level of power to lamps 21 and 31. The level of power can be adjustable in a continuous or stepped manner as indicated by pointers 51a and 52a on scales 51a and 52b, respectively.

With the above-described illumination means included in tester 10, the light from the source 31 is directed by diffuser 54 onto mirror 29 and reflected thereby toward the subject's eyes along with the light transmitted through the mirror from the targets 16 and 17. As a result, the subject at the viewing assembly 13 observes the targets through a uniform level of veiling illumination provided by the mirror. The uniform level is superimposed upon the light transmitted toward the vision by targets 16 and 17. Accordingly, the contrast ratio between the illumination level of the symbol regions and the illumination level of the background can be changed from that provided by the illuminated targets alone. Thus the contrast ratio becomes dependent upon the composite of the selected uniform level of veiling illumination (i.e., the selected illumination level of source 31) and the level of illumination of the target itself (i.e., the selected level of illumination of source 21). The aforesaid contrast ratio can be varied by varying the illumination level of either light source by means of their respective electrical sources 51 and 52. Here it should be noted that only the veiling light can be added to the portion of the field of view in alignment with the symbols since source 21 does not direct light from the dark symbols themselves toward the subject's eyes.

Figure 4:
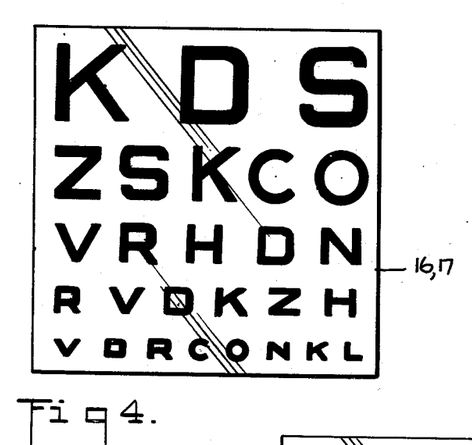
FIGS. 4–6 are representations of the appearance a test target of the apparatus of FIG. 1 for different light contrast ratios provided by the apparatus of the invention.
Figure 5:
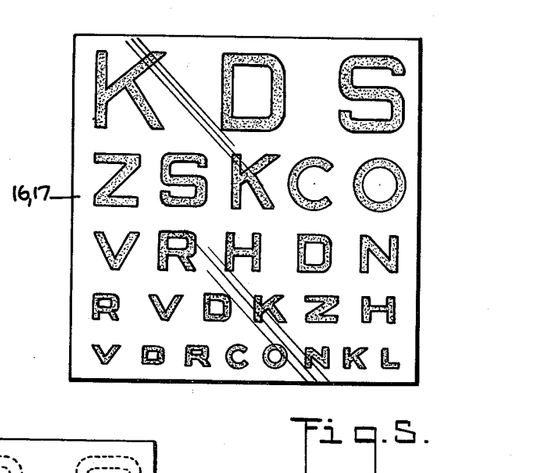
Figure 6:
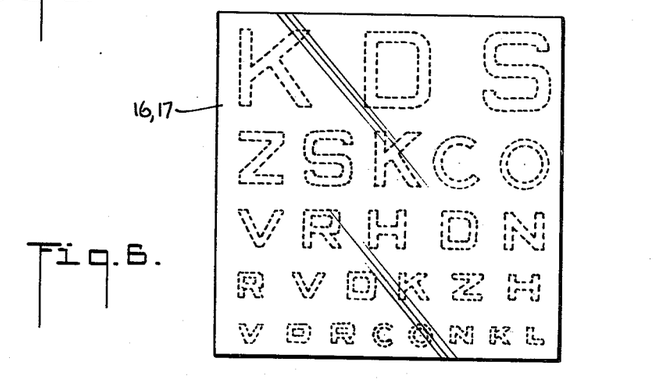

FIGS. 4, 5 and 6 show the targets 16 and 17 as viewed together by a viewer for three different increasing levels of illumination provided by the source 31. As can be seen by progressively increasing the level of veiling illumination to a maximum condition represented in FIG. 6 causes a decrease in the contrast ratio between the symbols and the background adjacent thereto. As a result it can be seen that the decreasing contrast ratio makes the symbols progressively less discernible.

In another embodiment of the invention (not shown), the position of the assembly of target assembly 14, diffusion screen 53 and source 21 relative to half-silvered mirror 29 can be exchanged for the position of the assembly veiling light source 31 and diffuser 54 with respect to mirror 29. In this embodiment the subject would also view the symbols over a range of contrast ratios resulting from a range of different levels of veiling light.

In using the tester 10 for testing of vision, the viewer would again be positioned at the viewing assembly 13 and the lamp 21 energized in order to illuminate the target. The viewer would then be asked to read the lines of the chart to establish his normal visual acuity. After the latter is established, the lamp 21 would then be decreased in intensity progressively or in steps until a contrast ratio condition is reached at which the viewer can only read the line above the previously read lowest line. At this point the latter line is no longer discernible because of the decreased contrast ratio between the symbols thereof and the background. Upon the occurrence of this condition, a record is made of the viewer's acuity corresponding to the new line and of the contrast corresponding to that acuity. In this way, a measure of the loss in acuity with respect to a given change in contrast ratio is obtained. This measure, in turn, can then be used to determine the various light scattering properties of the eye and any possible eye disorders associated therewith.

The tester 10 can also be used to test for the fusion potential of a subject's eyes. In this case, the member 15 is rotated to place dissimilar targets 18 and 19 into alignment with the viewing assembly 13. The lamp 21 is then illuminated. The optical wedges or prisms of the binocular optical assembly 41 are adjusted to diverage the line of sight of the subject with respect to targets 18 and 19 until a condition is reached at which some effort is required by the subject to view the symbols of a given line of the targets as a single fused image. The adjustment of the wedges or prisms is then held fixed for the subsequent test of the subject's fusion potential. Instead of diverging the lines of sight by wedges or prisms, divergence can be obtained by separating the targets.

After divergence is established a minimum level of veiling light is applied to reduce the contrast ratio. The tests are then repeated. The level of veiling light is subsequently increased progressively and thereby the contrast ratio is reduced progressively until a reduced contrast ratio condition is reached at which the subject can no longer fuse the symbols on the line of the charts which the subject could fuse, absent the veiling light. In this way the subject's fusion potential can be determined and measured. The occurrence of a loss of fusion can be detected by the report of the subject, by observations of the subject's eyes, or by electrical instrumentation capable of responding to eye movement.

The use of different levels of the veiling light can also be used in the testing of color vision, again using the principle of the change of contrast ratios of a target or targets bearing color symbols or forms in response to changes in the veiling light.

The vision tester can be used clinically to assess the change of cataract formation over a period of time or as a screening test for the quick detection of difficulties in vision of an unknow nature. Where any specific eye condition is associated with increased light scattering the vision tester enables any changes in the eye condition to be documented in a quantitative fashion over a long period of time.

In still another embodiment of the invention, the symbols of targets 16 and 17 can be formed from translucent material which is capable of plane polarizing light; such a construction would be in place of the use of symbols formed from opaque material. Between light source 21 and the symbols of polarizing material there is provided in this embodiment an adjustable polarizer 55. Light emitted by source 21 passes through polarizer 55 and then through the symbols of polarizing material on targets 16 and 17. By selectively positioning the polarizer, the plane of polarization of the light can be varied from a condition in which it can be transmitted by the polarizing material of the symbols to a condition in which it is blocked. As a result the darkness of the symbols can be varied, thereby varying the contrast ratio of the target as viewed by the subject. The background should remain constant to keep the composite brightness approximately constant. This arrangement can be used alone in testing the subject's vision under different contrast ratios or can be used in conjunction with a fixed level or a varying level of veiling light.

Figure 7:
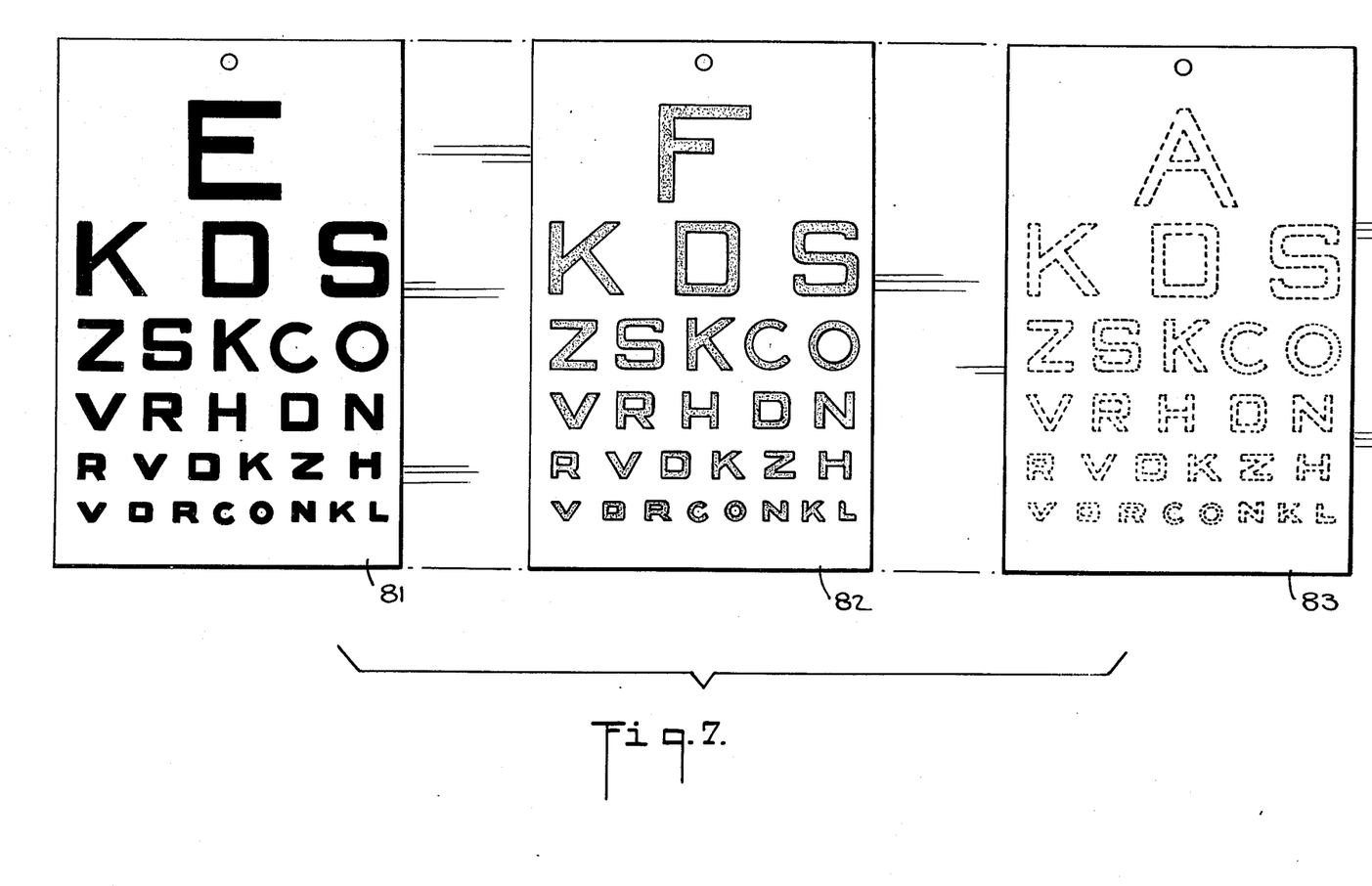
FIG. 7 comprises a representation of a plurality of test charts each having a different viewable contrast ratio.

FIG. 7 shows another embodiment of the present invention comprising means for presenting different viewable contrast ratios for use in vision testing. More particularly, such means comprises a plurality of test charts of which three charts, 81, 82 and 83, are shown by way of example. As illustrated, each of the charts is formed so as to have regions which are in the form of symbols of decreasing size arranged in rows analagous to the rows of a conventional eye chart. The format of the symbols of each different chart 81, 82 and 83 can be the same and thereby provide a common denominator in testing the viewer's visual acuity. The variable of the charts is that of a different contrast ratio for each chart. Thus, the symbols of each of charts 81, 82 and 83, in accordance with the invention, have a different degree of contrast with respect to those of the other charts. As shown in FIG. 7, by way of example, the background of each chart has the same reflectivity corresponding to that of a white smooth surface. In the illustrated case, the reflectivities $r_1$, $r_2$, and $r_3$ of the symbol regions of the regions of the respective charts, 81, 82 and 83 differ and are related to one another such that $r_1 < r_2 < r_3$.

As can be appreciated, the increasing reflectivity of the symbol regions of the charts will result in more light being reflected from the symbol regions; correspondingly, an increase of reflectively in the symbol region is accompanied by a decrease in the contrast ratio. As a result, illumination of the charts under normal lighting conditions will cause the chart 83 to exhibit less of a contrast ratio between its symbols and background than the charts 82 and 81 and the chart 82 less of a contrast ratio than the chart 81. Accordingly, the charts 81, 82 and 83 can be used to measure a decrease in acuity for a given change in the contrast ratio.

The charts are used together and a viewer is first asked to read the lowest line on the chart having the greatest contrast ratio, such as chart 81 in the illustrated case. Then the viewer is asked to read the corresponding line on the remaining eye charts until the viewer reaches a chart at which he can no longer read the corresponding line but only the line above. At this point, the viewer's measured change in acuity can be ascertained in relation to the change in contrast ratio from the contrast ratio values of the charts.

What is claimed is:

1. Apparatus for testing the vision of a subject's eyes comprising:

at least one test target having differing optical characteristics thereover disposed within the apparatus for viewing by a subject, the test target being disposed in the field of view of the subject when the eyes of the subject are located at a predetermined viewing position which is at a predetermined distance from the test target, the test target when being illuminated directing a light image of the test target through the field of view of the subject and towards the subject's eyes, the test target when illuminated providing a region thereon having a level of illumination different from the level of illumination of the remaining background portion of the test target in response to the differing optical characteristics thereof, the difference in the levels of illumination establishing a contrast ratio in the light image from the illuminated test target which can be observed by the subject in the field of view;

means disposed within the apparatus for illuminating the test target;

means disposed within the apparatus for providing a source of diffused veiling illumination;

means disposed within the apparatus for directing toward the subject's eyes a level of veiling illumination derived from the diffused veiling illumination of the source thereof, the veiling illumination directing means including a member disposed between the at least one test target and the predetermined viewing position at which the eyes of the subject can be disposed, said member extending across all portions of the field of view of the subject and the level of diffused veiling illumination correspondingly extending throughout all portions of the field of view between said member and the predetermined viewing position, said member being operative to transmit the light image of the test target through the field of view towards the predetermined viewing position and to direct the diffused veiling illumination from the source thereof through the field of view toward the predetermined position, said member transmitting the light image of the test target and directing the diffused veiling illumination substantially coextensively and in alignment in the field of view from said member to the predetermined viewing position, the diffused veiling illumination being directed independently of the illumination of the test target, the interaction of the diffused veiling illumination with the light image from the illuminated test target causing a change in the contrast ratio of the light image from the illuminated test target which can be observed by the subject in the field of view presented to the subject's eyes, the change in the contrast ratio being a variable in the testing of the subject's vision.

2. Apparatus in accordance with claim 1 and further comprising means connected to the means for directing a level of veiling illumination for varying the level of veiling illumination over a predetermined range of levels, the predetermined range of levels providing a plurality of changes in the contrast ratio.

3. Apparatus in accordance with claim 2 in which said means for varying the level of veiling illumination over a predetermined range varies the level of veiling illumination in predetermined steps with each step providing a different contrast ratio.

4. Apparatus is accordance with claim 1 and further comprising means connected to the means for illuminating the test target for varying the illuminating level thereof over a predetermined range, the varying illumination levels providing a plurality of different contrast ratio.

5. Apparatus in accordance with claim 1 in which said means for directing a level of veiling illumination toward the subject's eyes comprises:

a partially light-reflective and partially light-transmissive member extending across the field of view, the partially reflective portion of the member being adapted to reflect one of the illumination of the illuminated test target by the illuminating means and the veiling illumination applied to the member toward the subject's eyes, the partially transmissive portion of the member being adapted to transmit the other one of the illumination of the illuminated test target by the illuminating means and the veiling illumination applied to the member toward the subject's eyes; and a source of the veiling illumination adapted to be applied toward the member, the member enabling the subject to view the composite of the veiling illumination and the illuminated test target.

6. Apparatus in accordance with claim 5 in which said partially light-reflective and partially light-transmissive member is a semi-transparent mirror.

7. Apparatus in accordance with claim 6 in which the source of light is disposed to one side of the field of view and in which the semi-transparent mirror is in the form of a plate having its oppositely disposed sides inclined with respect to the direction of the illumination extending from the illuminated test target and having its reflective portion in alignment with the source of light to reflect light from the source toward the subject's eyes when the subject observes the field of view.

8. Apparatus in accordance with claim 1 in which:

the region of the target is opaque and the background portion of the test target is adapted to present light to the field of view when the test target is illuminated.

9. Apparatus in accordance with claim 8 in which:
the background portion of the test target is translucent, and the means for illuminating the test target illuminates the test target in a direction extending therethrough toward the subject's eyes.

10. Apparatus in accordance with claim 8 in which the test target includes:
a plurality of different opaque regions of diminishing size, the regions being arranged in a predetermined order related to the diminishing of the sizes of the regions.

11. Apparatus in accordance with claim 5 and further comprising:
an elongated housing, the test target and the means for illuminating the test target being disposed adjacent one end portion of the interior of the housing and the partially light-reflective and partially light-transmissive member extending across the central portion of the housing with the source of light therefor being disposed in the housing adjacent thereto; and
a viewing assembly extending into the housing at the opposite end portion thereof and an alignment with the partially light-reflective and partially light-transmissive member and the test target for enabling the test target be viewed through the member.

12. Apparatus in accordance with claim 11 in which the test target includes first and second target portions each facing the viewing assembly and being arranged in a side-by-side relationship extending in a horizontal direction.

13. Apparatus in accordance with claim 11 in which the viewing assembly includes:
first and second apertures which are spaced apart horizontally with respect to one another at a distance subsantially equal to the interpupillary distance of a test subject's eyes, the apertures providing a region of observation into the housing for the eyes of the test subject; and
binocular optical means in alignment with the first and second apertures for directing the eyes of the subject along different predetermined lines of sight extending toward the test target; and
means for establishing a predetermined degree of divergence between the predetermined lines of sight by testing the subject's fusion potential.

14. Apparatus in accordance with claim 13 in which said viewing assembly further includes:
a mask for selectively blocking one of the first and second apertures; and
means for selectively positioning the mask in any one of the positions in which the mask blocks the first aperture, blocks the second aperture, and is clear of the first and second apertures, the mask enabling the viewing of the test target selectively by either eye of the subject.

15. Apparatus for testing the vision of a subject's eyes under varying contrast ratios comprising:
a test target having a background portion and test indicia thereon, the indicia being formed by translucent material which is adapted to plane polarize light transmitted therethrough;
a source for transmitting light through the translucent material forming the indicia in a direction extending toward the eyes of the subject;
means for plane polarizing the light transmitted by the source; and
means for selectively positioning the polarizing means to determine the orientation of the plane of polarization, the interaction between the light polarized by the polarizing means and the plane of polarization of the material forming the indicia enabling the amount of light transmitted therethrough to be selected and thereby contrast ratio of the test target.

16. A method for testing the vision of a subject's eyes comprising the steps of:
providing at least one test target having differing optical characteristics thereover disposed for viewing by a subject, the test target being disposed in the field of view of the subject when the eyes of the subject are located at a predetermined viewing position which is at a predeterminted distance from the test target, the test target when being illuminated directing a light image of the test target through the field of view of the subject and towards the subject's eyes, the test target when illuminated providing a region thereon having a level of illumination different from the level of illumination of the remaining background portion of the test target in response to the differing optical characteristics thereof, the difference in the levels of illumination establishing a contrast ratio in the light image from the illuminated test target which can be observed by the subject in the field of view;
illuminating the test target;
providing a source of diffused veiling illumination;
directing toward the subject's eyes a level of veiling illumination derived from the diffused veiling illumination of the source thereof, the veiling illumination being directed from a member disposed between the at least one test target and the predetermined viewing position at which the eyes of the subject can be disposed, said member extending across all portions of the field of view of the subject and the level of veiling illumination correspondingly extending throughout all portions of the field of view between the test target and the predetermined viewing position, said member being operative to transmit the light image of the test target through the field of view towards the predetermined viewing position and to direct the diffused veiling illumination from the source thereof disposed without the field of view through the field of view towarded the predetermined position, said member transmitting the light image of the test target and directing the veiling illumination substantially coextensively and in alignment in the field of view from said member to the predetermined viewing position, the veiling illumination being directed independently of the illumination of the test target, the interaction of the veiling illumination with the light image from the illuminated test target causing a change in the contrast ratio of the light image from the illuminated test target which can be observed by the subject in the field of view presented to the subject's eyes, the change in the contrast ratio being a variable in the testing of the subject's vision.

17. A method in accordance with claim 16 and further comprising the step of varying the level of veiling illumination over a predetermined range of levels, the predetermined range of levels providing a plurality of changes in the contrast ratio.

18. A method in accordance with claim 16 and further comprising varying the illuminating level of the test target over a predetermined range, the varying illumination levels providing a plurality of different contrast ratios.

19. A method in accordance with claim 16 and further including the step of varying the illuminating of the field of view with additional illumination directed toward the subject, whereby the contrast ratio is varied.

20. A method in accordance with claim 16 and further including the step of varying the illuminating of the test target, whereby the contrast ratio is varied.

21. A method in accordance with claim 16 in which the test target includes a plurality of the region in the form of symbols of diminishing size and the method further includes the step of:

varying the illuminating of the entire field of view with additional illumination directed toward the subject until the smallest symbol observable in the absence of the illuminating of said field of view just becomes one of discernible or non-discernible.

22. A method in accordance with claim 16 in which the target includes first and second target portions which are separated and which are in a side-by-side relationship; and in which the step of presenting the test target comprises presenting the first target portion to only one eye of the subject and the presenting of the second target portion to only the other eye of said subject for causing the first and second target portions to be viewed by the subject as a single fused target.

* * * * *

UNITED STATES PATENT AND TRADEMARK OFFICE
CERTIFICATE OF CORRECTION

PATENT NO. : 4,155,632
DATED : May 22, 1979
INVENTOR(S) : Myron L. Wolbarsht

It is certified that error appears in the above-identified patent and that said Letters Patent are hereby corrected as shown below:

Column 2, line 19, delete "Kerr" and insert --KERR--

Column 5, line 56, delete "locking" and insert --looking--

Column 6, line 11, delete "veling" and insert --veiling--

Column 6, line 47, delete "21" and insert --31--

Column 6, line 61, delete second occurrence of "51a" and insert --51b--

Column 11, line 25, delete "an" and insert --in--

Column 11, line 39, delete "subsantially" and insert --substantially--

Column 12, line 18, delete "predeterminted" and insert --predetermined--

Column 12, line 50, delete "towarded" and insert --toward--

Signed and Sealed this

Eighteenth Day of September 1979

[SEAL]

Attest:

Attesting Officer

LUTRELLE F. PARKER
Acting Commissioner of Patents and Trademarks